US012708636B2

(12) United States Patent
Widberg et al.

(10) Patent No.: US 12,708,636 B2
(45) Date of Patent: Aug. 18, 2026

(54) NUTRITIONAL COMPOSITIONS CONTAINING PHOSPHATIDYLSERINE POWDER

(71) Applicant: FRUTAROM LIMITED, Migdal Haemeq (IL)

(72) Inventors: Asher Widberg, Haifa (IL); Yael Herzog, Gesher HaZiv (IL)

(73) Assignee: FRUTAROM LIMITED, Migdal Haemeq (IL)

( * ) Notice: Subject to any disclaimer, the term of this patent is extended or adjusted under 35 U.S.C. 154(b) by 0 days.

(21) Appl. No.: 17/817,747

(22) Filed: Aug. 5, 2022

(65) Prior Publication Data

US 2023/0105546 A1 Apr. 6, 2023

Related U.S. Application Data

(63) Continuation of application No. 15/328,824, filed as application No. PCT/IB2015/001772 on Jul. 23, 2015, now abandoned.

(60) Provisional application No. 62/029,109, filed on Jul. 25, 2014.

(51) Int. Cl.

| | |
|---|---|
| ***A61K 31/685*** | (2006.01) |
| ***A23G 3/40*** | (2006.01) |
| ***A23J 7/00*** | (2006.01) |
| ***A23L 33/00*** | (2016.01) |
| ***A23L 33/10*** | (2016.01) |
| ***A61K 9/16*** | (2006.01) |
| ***C07F 9/10*** | (2006.01) |

(52) U.S. Cl.

CPC .............. *A61K 31/685* (2013.01); *A23G 3/40* (2013.01); *A23J 7/00* (2013.01); *A23L 33/00* (2016.08); *A23L 33/10* (2016.08); *A23L 33/40* (2016.08); *A61K 9/1611* (2013.01); *C07F 9/103* (2013.01); *A23V 2002/00* (2013.01)

(58) Field of Classification Search

CPC ..... A61K 31/685; A61K 9/1611; A23L 33/00; A23L 33/10; A23L 33/40; A23G 3/40; A23J 7/00; C07F 9/103; A23V 2002/00

See application file for complete search history.

(56) References Cited

U.S. PATENT DOCUMENTS

| | | | | |
|---|---|---|---|---|
| 7,067,292 B2 | 6/2006 | Hoppe et al. | | |
| 8,324,187 B2 * | 12/2012 | Plat | C07F 9/103 | 424/439 |
| 2006/0257490 A1 | 11/2006 | Cremer et al. | | |
| 2009/0238880 A1 * | 9/2009 | Ulm | A61P 31/10 | 514/183 |
| 2012/0160944 A1 * | 6/2012 | Dodd | A61K 31/53 | 241/30 |
| 2013/0131007 A1 | 5/2013 | Brown | | |

FOREIGN PATENT DOCUMENTS

| | | |
|---|---|---|
| EP | 0776976 A2 | 6/1997 |
| JP | 2013143913 A | 7/2013 |
| WO | 2005027822 A2 | 3/2005 |

OTHER PUBLICATIONS

Product Information for "Phosphatidylserine in Pharma Grade" from Biolla Chemicals; downloaded Jun. 27, 2024 from https://biollachemicals.com/product/phosphatidylserine-powder-cas-51446-62-9 (Year: 2024).*

European Official Communication dated Jun. 18, 2019 with Third-Party Observations filed in counterpart European Patent Application No. 15781413.8; 53 pgs.

Collins Dictionary online; definition of 'dispersible', downloaded Jul. 1, 2021 from https://www.collinsdictionary.com/us/dictionary/english/dispersible. (Year: 2021).

Official Communication dated Sep. 17, 2019 issued in counterpart European Patent Application No. 15781413.8; 3 pgs.

LE CI-PS® 20P by CONNOils—Food, Beverage & Nutrition. Found at: https://www.ulprospector.com/en/na/Food/Detail/4364/330971/LECI-PS-20P Feb. 16, 2018 downloaded Feb. 16, 2018. (Year: 2018).

* cited by examiner

*Primary Examiner* — Michael P Cohen

(74) *Attorney, Agent, or Firm* — Fox Rothschild LLP

(57) ABSTRACT

Phosphatidylserine powder compositions of the present invention were found to provide more homogeneous dispersion and demonstrate reduced sedimentation, compared to conventional phosphatidylserine powders, when mixed without processing by high pressure homogenization in water or other liquids. The composition of the present invention comprises phosphatidylserine and at least 80% (w/w) of the composition has a particle size of 500 microns or less. Nutritional, nutraceutical, or pharmaceutical compositions including the phosphatidylserine powder compositions of the present invention are also provided. Process for preparing phosphatidylserine powder compositions according to the present invention is also provided and includes sieving.

16 Claims, No Drawings

NUTRITIONAL COMPOSITIONS CONTAINING PHOSPHATIDYLSERINE POWDER

FIELD OF THE INVENTION

The present invention refers to PS preparations with predetermined particle size.

BACKGROUND OF THE INVENTION

Phosphatidylserine (PS), which is the main acid phospholipid in mammalian plasma membrane, has been shown to play a key role in the functioning of neuron membranes and to alter multiple neurochemical systems (See Vance et al. Metabolism and functions of phosphatidylserine. Prog. Lipid Res. 2005; 44:207-234). Supplementation of PS to animal models has been shown to attenuate neuronal effects of aging, as well as restoring normal memory in a range of tasks. In human, administration of PS to subjects with age-associated memory impairment, as well as to mild cognitive impairment patients, resulted with a consistent improvement of performance in memory tests. Studies conducted on children and adolescents tested the effects of PS supplementation on various cognitive and behavior aspects. These studies attest to the ability of PS to improve memory, attention and more in children, as well as to the safety of PS in children (See Hirayama et al. Effect of phosphatidylserine administration on symptoms of attention-deficit/hyperactivity disorder in children. AgroFOOD industry hi-tech. 2006; 17:32-36).

Unfortunately, mixing conventional PS powder preparations or PS preparations in which more than 20% (w/w) of the powder has a particle size of above 500 microns with nutritional or nutraceutical compositions often result in a non-homogeneous dispersion that contains floating visible particles and/or sediments and/or interferes with the structure of chewable matrixes.

Additional problem is the reduced stability of conventional PS powder in water medium and other matrixes.

Previous solutions for the non-homogeneous problem include adding the PS powder in the early preparation stage of certain nutritionals or nutraceutical powders. In such cases, the preparation is based on a high pressure homogenization in water followed by spray drying to obtain the dry powder. The addition of the PS powder before pressure homogenization will ensure that the final powder will have the required properties when mixed with an aqueous solution. Nevertheless, this order of preparation exposes the PS powder to a long and harmful exposure to oxygen, heat, and water thereby increasing the likelihood of degradation and oxidation of the PS.

Furthermore, in large scale production, adding the PS powder prior to spray drying stage causes logistic problems and creates difficulties to manufacturers. Adding the PS to the final nutritional or nutraceutical product, in a dry blending stage, may give the manufacturers the ability to get high flexibility between batches and avoid cross-contaminates.

The present invention provides PS preparations with predetermined particle size that may be added to final nutritional, nutraceutical, or pharmaceutical compositions. These novel PS preparations have increased stability, are homogenous in certain water mediums, and enable the stability of solid and elastic mediums.

SUMMARY OF THE INVENTION

The present invention provides a phosphatidylserine powder composition comprising a phosphatidylserine; wherein at least 80% (w/w) of the phosphatidylserine powder composition has a particle size of 500 microns or less. Preferably the particle size of the phosphatidylserine powder composition is 400 microns or less, more preferably 350 microns or less, even more preferably 300 microns or less, even more preferably 250 microns or less, even more preferably 200 microns or less, and most preferably 150 microns or less. The percentage by weight of the phosphatidylserine powder that satisfies the aforementioned particle size is preferably at least 85% (w/w), more preferably at least 90% (w/w), even more preferably at least 95% (w/w), and most preferable at least 97% (w/w). Preferably less than 20% (w/w) of the powder has particle size above 500 microns, at times less than 15% (w/w) at times less than 10% (w/w), at times less than 8% (w/w), at times less than 5% (w/w), at times less than 3% (w/w) and at times less than 1% (w/w).

In certain other non-limiting embodiments of the present invention, the phosphatidylserine powder composition is prepared from a natural source, synthetic source, semisynthetic source, or a combination thereof. In certain other non-limiting embodiments of the present invention, the phosphatidylserine is prepared using a monophasic reaction, a bi-phasic reaction, or a combination thereof. In certain other non-limiting embodiments of the present invention, the phosphatidylserine is prepared using a mono-phasic reaction and purified using an organic solvent. In certain other non-limiting embodiments of the present invention, the organic solvent is an alcohol solvent. In certain other non-limiting embodiments of the present invention, the phosphatidylserine is prepared using a bi-phasic reaction. In certain other non-limiting embodiments of the present invention, when mixed in water without processing by high pressure homogenization, the powder composition disperses more homogeneously and demonstrates reduced sedimentation in comparison to conventional PS powder preparations, or with a PS preparation in which more than 20% (w/w) of the PS preparation has a particle size of above 500 microns. In certain other non-limiting embodiments of the present invention, the powder composition is mixed with a powder nutritional, nutraceutical, or pharmaceutical composition to form a mixture, and when the mixture is mixed with water without processing by high pressure homogenization, the mixture disperses more homogeneously and demonstrates reduced sedimentation compared to a mixture of a powder nutritional, nutraceutical, or pharmaceutical composition and conventional PS powder preparations or a PS preparation in which more than 20% (w/w) of the PS preparation has a particle size of above 500 microns. In certain other non-limiting embodiments of the present invention, the powder composition when mixed without processing by high pressure homogenization with a liquid nutritional, nutraceutical, or pharmaceutical composition more homogeneously disperses and demonstrates reduced sedimentation compared to conventional PS powder preparations, or a PS preparation in which more than 20% (w/w) of the PS preparation has a particle size of above 500.

The present invention also provides a nutritional, pharmaceutical, or nutraceutical composition or a functional or medical food comprising any one of the phosphatidylserine powder compositions disclosed above.

In certain other non-limiting embodiments of the present invention, the nutritional or nutraceutical composition is a biscuit, pastry, cake, bread, cereal, bar, snack, pill, tablet, pellets, dragées, capsule, soft gel, syrup, baby formula, adult formula, medical nutrition product, candy, gummy, or confectionary. In certain other non-limiting embodiments of the present invention, the nutritional, nutraceutical, or pharmaceutical composition maintains a uniform appearance. In certain other non-limiting embodiments of the present invention, the nutritional, nutraceutical, or pharmaceutical composition maintains elastic stability during storage. In certain other non-limiting embodiments of the present invention, the bulk density of the phosphatidylserine powder composition in the nutritional, nutraceutical, or pharmaceutical composition is 0.2 to 0.7 g/ml. In certain other non-limiting embodiments of the present invention, the dosage unit of the phosphatidylserine powder composition in the nutritional, nutraceutical, or pharmaceutical composition is 10 mg to 1000 mg. In certain other non-limiting embodiments of the present invention, the nutritional, nutraceutical, or pharmaceutical composition is a liquid. In certain other non-limiting embodiments of the present invention, the nutritional, nutraceutical, or pharmaceutical composition is a powder. In certain other non-limiting embodiments of the present invention, the nutritional, nutraceutical, or pharmaceutical composition contains at least one protein and at least one carbohydrate. In certain other non-limiting embodiments of the present invention, the phosphatidylserine powder is at least 0.05% (w/w) of the nutritional, nutraceutical, or pharmaceutical composition. In certain other non-limiting embodiments of the present invention, the nutritional, nutraceutical, or pharmaceutical composition comprises a phosphatidylserine powder composition prepared from a natural source, synthetic source, semisynthetic source, or a combination thereof. In certain other non-limiting embodiments of the present invention, the nutritional, nutraceutical, or pharmaceutical composition comprises a phosphatidylserine powder composition prepared using a monophasic reaction, a bi-phasic reaction, or a combination thereof. In certain other non-limiting embodiments of the present invention, the nutritional, nutraceutical, or pharmaceutical composition comprises a phosphatidylserine powder composition prepared using a mono-phasic reaction and purified using an organic solvent. In certain other non-limiting embodiments of the present invention, the organic solvent is an alcohol solvent. In certain other non-limiting embodiments of the present invention, the nutritional, nutraceutical, or pharmaceutical composition further comprises another phospholipid.

The present invention also provides a process for preparing a phosphatidylserine powder preparation comprising sieving a phosphatidylserine powder, wherein the resulting phosphatidylserine powder preparation is any one of the phosphatidylserine powder compositions disclosed above. In certain other non-limiting embodiments of the present invention, the process comprises preparing the phosphatidylserine powder composition from a natural source, synthetic source, semisynthetic source, or a combination thereof. In certain other non-limiting embodiments of the present invention, the process comprises preparing the phosphatidylserine powder composition using a monophasic reaction, a bi-phasic reaction, or a combination thereof. In certain other non-limiting embodiments of the present invention, the process comprises preparing the phosphatidylserine powder composition using a mono-phasic reaction. In certain other non-limiting embodiments of the present invention, the process comprises preparing the phosphatidylserine powder composition using a bi-phasic reaction.

In certain other non-limiting embodiments of the present invention, the process for preparing a phosphatidylserine powder preparation further comprises a dry milling step wherein the phosphatidylserine is dried then milled to obtain a dry milled powder. In certain other non-limiting embodiments of the present invention, the phosphatidylserine is milled together with silicon dioxide, preferably 2% silicon dioxide. In certain other non-limiting embodiments of the present invention, the dry milled powder is a free flowing powder. In certain other non-limiting embodiments of the present invention, the process for preparing a phosphatidylserine powder preparation further comprises a purification step using an organic solvent. In certain other non-limiting embodiments of the present invention, the organic solvent is an alcohol solvent. In certain other non-limiting embodiments of the present invention, the alcohol solvent is a C1-C6 alcohol. In certain other non-limiting embodiments of the present invention, the alcohol solvent is a C2-C3 alcohol.

DETAILED DESCRIPTION OF THE INVENTION

The present invention provides PS powder composition comprising a PS in which the majority of the particles have a predetermined particle size.

According to some embodiments the predetermined particle size is 500 microns or less, preferably 400 microns or less, preferably 450 microns or less, more preferably 350 microns or less or 300 microns or less, even more preferably 250 microns or less or 200 microns or less, and most preferably 150 microns or less.

According to some embodiments at least 80% (w/w) of the particles in the PS powder preparation have the predetermined size, at times at least 85% (w/w), at times at least 90% (w/w), at times at least 95% (w/w), at times at least 97% (w/w) and at times at least 99% (w/w).

The present invention provides phosphatidylserine powder composition comprising a phosphatidylserine, wherein at least 80% (w/w), at times at least 85% (w/w), at times at least 90% (w/w), at times at least 95% (w/w), at times at least 97% (w/w), and at times at least 99% (w/w) of the phosphatidylserine powder composition has a particle size of 500 microns or less.

The present invention provides phosphatidylserine powder composition comprising a phosphatidylserine, wherein less than 20% (w/w), at times less than 15% (w/w), at times less than 10% (w/w), at times less than 8% (w/w), at times less than 5% (w/w), at times less than 3% (w/w) and at times less than 1% (w/w) of the phosphatidylserine powder preparation has particle size of above 500 microns.

According to some embodiments at least 80% (w/w), at times at least 85% (w/w), at times at least 90% (w/w), at times at least 95% (w/w), at times at least 97% (w/w), and at times at least 99% (w/w) of the phosphatidylserine powder composition has a particle size of 450 microns or less.

According to some embodiments at least 80% (w/w), at times at least 85% (w/w), at times at least 90% (w/w), at times at least 95% (w/w), at times at least 97% (w/w), and at times at least 99% (w/w) of the phosphatidylserine powder composition has a particle size of 400 microns or less.

According to some embodiments at least 80% (w/w), at times at least 85% (w/w), at times at least 90% (w/w), at times at least 95% (w/w), at times at least 97% (w/w), and at times at least 99% (w/w) of the phosphatidylserine powder composition has a particle size of 350 microns or less.

According to some embodiments at least 80% (w/w), at times at least 85% (w/w), at times at least 90% (w/w), at times at least 95% (w/w), at times at least 97% (w/w), and at times at least 99% (w/w) of the phosphatidylserine powder composition has a particle size of 300 microns or less.

According to some embodiments at least 80% (w/w), at times at least 85% (w/w), at times at least 90% (w/w), at times at least 95% (w/w), at times at least 97% (w/w) and at times at least 99% (w/w) of the phosphatidylserine powder composition has a particle size of 250 microns or less.

According to some embodiments at least 80% (w/w), at times at least 85% (w/w), at times at least 90% (w/w), at times at least 95% (w/w), at times at least 97% (w/w) and at times at least 99% (w/w) of the phosphatidylserine powder composition has a particle size of 200 microns or less.

According to some embodiments at least 80% (w/w), at times at least 85% (w/w), at times at least 90% (w/w), at times at least 95% (w/w), at times at least 97% (w/w) and at times at least 99% (w/w) of the phosphatidylserine powder composition has a particle size of 150 microns or less.

Particle size was tested based on Particle Size Distribution Estimation by Analytical Sieving USP 786 method I. Using this test method, particle size is represented by the minimum square aperture through which the particle can pass. For the purposes of the present invention, this method may be used to determine particle size irrespective of what percentage by weight of the sample has a particle size larger than 75 microns. Mechanical sieving was performed using 100 grams of a dry powder sample. The sample was then sieved using US Sieve number 60 or EU sieve number 250. This sieve selection is able to test for a particle size of 250 microns or less. One of ordinary skill in the art is able to select the proper sieve in order to test for a variety of particle sizes. The cumulative percentage by weight of sample passing through the sieve is the percentage by weight of the sample having a particle size (or less) of the sieve size opening for the selected sieve. Samples were agitated using manual tapping as the agitation method and agitated for five minutes. Agitation cycles were repeated until the weight of the test sieved did not change by more than 5% of the previous weight on that sieve. Particle size results were disregarded if particles were observed to be aggregated after agitation and testing was repeated.

As used herein the terms "phosphatidylserine" and "PS" used interchangeably, should be understood to encompass a lipid of the general formula:

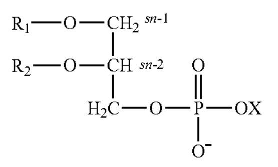

wherein the substituents, $R_1$ (substituent on position sn-1) and $R_2$ (substituent on position sn-2), are independent of each other and are selected from H or an acyl group selected from saturated, mono-unsaturated and polyunsaturated fatty acids and X is serine, i.e. $—CH_2CH(COOH)NH_2$.

The sn-1 and sn-2 positions as used herein and as indicated in above formula, refer to the respective carbon atoms on the glycerol backbone wherein $R_1$ and $R_2$, are substituted on the corresponding acyl groups.

In the present invention, the terms "substituted" and its lingual equivalents and the term "conjugated" and its lingual equivalents are interchangeably used and should be understood to encompass a fatty acid acyl covalently attached to the glycerophospholipid backbone of a serine glycerophospholipid of the invention. As noted above, the fatty acid may be attached to the sn-1 and/or sn-2 positions.

As used herein, the term "fatty acid" should be understood to encompass a carboxylic acid with a long unbranched aliphatic tail (chain), which is either saturated or unsaturated having one unsaturated bond (mono-unsaturated fatty acids) or two or more unsaturated bonds (poly-unsaturated fatty acids). When referring to a "fatty acid acyl" it should be understood to encompass an —C(═O)—R radical wherein R is a long unbranched aliphatic tail, which is either saturated or unsaturated having one unsaturated bond (mono-unsaturated fatty acids) or two or more unsaturated bonds (poly-unsaturated fatty acids).

Non-limiting examples of saturated fatty acids include: Butyric acid (Butanoic acid, C4:0), Caproic acid (Hexanoic acid, C6:0), Caprylic acid (Octanoic acid, C8:0), Capric acid (Decanoic acid, C10:0), Lauric acid (Dodecanoic acid, C12:0), Myristic acid (Tetradecanoic acid, C14:0), Palmitic acid (Hexadecanoic acid, C16:0), Stearic acid (Octadecanoic acid, C18:0), Arachidic acid (Eicosanoic acid, C20:0), Behenic acid (Docosanoic acid C22:0).

Non-limiting examples of unsaturated fatty acids include: Myristoleic acid (C14:1, ω-5), Palmitoleic acid (C16:1, ω-7), Oleic acid (C18:1, ω-9), Linoleic acid (C18:2, ω-6), Linolenic acid (C18:3) [Alpha-linolenic acid (C18:3, ω-3), Gamma-linolenic acid (C18:3, ω-6)], Eicosenoic acid (C20:1, ω-9), Arachidonic acid (C20:4, ω-6), Eicosapentaenoic acid (C20:5, ω-3), Erucic acid (C22:1, ω-9), Docosapentanoic acid (C22:5, ω-3) and Docosahexaenoic acid (C22:6, ω-3), Nervonic acid (C24:1, ω-9).

When referring to a " . . . [fatty acid] conjugated to PS . . . ", it should be understood to encompass a PS wherein a fatty acid acyl is conjugated at position sn-1 and/or position sn-2 of the phospholipid backbone (through the glycerol oxygen atom). In one embodiment a fatty acid is conjugated at position sn-1, and position sn-2 is either unsubstituted (e.g. having a hydrogen atom on the glycerol oxygen) or substituted with an acyl group selected from saturated, mono-unsaturated and polyunsaturated fatty acids, which may be the same or different from the substitution on position sn-1.

In another embodiment a fatty acid is conjugated at position sn-2 and position sn-1 is either unsubstituted (e.g. having a hydrogen atom on the glycerol oxygen) or substituted with an acyl group selected from saturated, mono-unsaturated and polyunsaturated fatty acids, which may be the same or different from the substitution on position sn-2.

The present invention also provides a nutritional, pharmaceutical, or nutraceutical composition or a functional or medical food comprising any one of the phosphatidylserine powder compositions disclosed above.

The subject invention envisages that PS powder preparations with particle size of 500 micron or less advantageously provide better stability and homogenous properties when incorporated into nutritional, nutraceutical, or pharmaceutical compositions in comparison with PS preparations with particle size of more than 500 micron.

Furthermore, the invention provides PS preparations with particle size of 500 micron or less which are produced through a monophasic transphosphatidylation process, and advantageously possess even better stability and homogenous properties when incorporated into nutritional, nutraceutical, or pharmaceutical compositions, in comparison with PS powder of the same particle size which is produced through a bi-phasic transphosphatidylation process.

The invention is advantageous compared to other existing commercial PS powders. Upon mixing with powder nutritional, nutraceutical, or pharmaceutical compositions and dispersion in water, commercial PS powders/PS preparations in which more than 20% (w/w) of the powder has a particle size of above 500 microns tend to form non-homogenous mixtures with floating particle and sediments and reduced PS stability. Similar non-homogenous mixtures with reduced PS stability are also formed upon mixing commercial PS powders directly with water based nutritional, nutraceutical, or pharmaceutical compositions. Furthermore, the addition of conventional PS powders or PS preparations in which more than 20% (w/w) of the powder has a particle size of above 500 microns to chewable matrixes, such as candies or gummies, tend to reduce the elasticity and stability of said chewable nutritional, nutraceutical, or pharmaceutical compositions.

A nutritional composition as used herein can be any nutritional composition including, but not limited to: human milk fat substitute, infant formula, adult formula, dairy product, including milk and dairy drinks, milk powder, drinks, shakes, ice cream, biscuit, soy product, bakery, pastry, bread, cake, sauce, soup, prepared food, including prepared mashed vegetables and/or fruits, frozen food, condiment, confectionary, oil, fat, margarine, spread, filling, meat product, cereal, instant product, instant drink product, infant food, toddler food, bar, snack, candy, and chocolate product.

A nutraceutical composition as used herein can be any nutraceutical, which can be any substance that may be considered as a food or part of a food and provides medical or health benefits, including the prevention and treatment of diseases or disorders. Such nutraceutical compositions include, but are not limited to: a food additive, a food supplement, a dietary supplement, genetically engineered foods (such as for example vegetables, herbal products, and processed foods such as cereals, soups, and beverages), stimulant functional food, clinical nutrition product, medical food, and pharmafood. Dietary supplements may be delivered in the form of soft gel capsules, tablets, syrups, and other known dietary supplement delivery systems.

The pharmaceutical or nutraceutical compositions may be in any of the many dosage delivery forms commonly used in the art. Pharmaceutical or nutraceutical compositions suitable for oral administration may be presented as discrete dosage units (such as pills, tablets, pellets, dragées, capsules, or softgel), as a powder or granule, or as a solution, suspension, syrup, or elixir.

In a preferred embodiment the, nutraceutical composition is a powder dietary supplement or functional food intended to be mixed with water, water based dietary supplement, water based functional food, or a chewable dietary supplement or functional food such as candy or gummy.

Preferably the nutritional or nutraceutical compositions further contain at least one protein and at least one carbohydrate components.

A functional food as used herein can be any functional food, including, but not limited to, dairy product, ice-cream, biscuit, soy product, bakery, pastry, cakes and bread, instant product, sauce, soup, prepared food, frozen food, condiment, confectionary, oils and fat, margarine, spread, filling, cereal, instant product, drinks and shake, infant food, bar, snack, candy and chocolate product.

Dietary supplements may be delivered in the form of pills, tablets, pellets, dragées, capsules, soft gels, sachet, syrups, and other known dietary supplement delivery systems.

According to one embodiment the PS powder composition of the invention is added to medical foods.

A medical food as used herein is specially formulated and intended for the dietary management of a disease/disorder that has distinctive nutritional needs that cannot be met by normal diet alone.

According to one embodiment the present invention provide PS powder with bulk density with the range of 0.2-0.7 gr/ml, preferably 0.3-0.6 gr/ml, more preferably 0.35-0.55 gr/ml and most preferably 0.4-0.5 gr/ml.

In one embodiment, the PS powder preparation contains at least 10% w/w PS out of the preparation, preferably at least 20%, more preferably at least 30% or 40%, even more preferably at least 50% or 60% and most preferably at least 70% or 80%.

According to another embodiment the PS concentration out of the nutraceutical composition is between 0.05% to 10% W/W, preferably 0.1% to 7%, more preferably 0.5% to 5% and most preferably 1% to 4%.

According to a further embodiment the PS dose in a nutraceutical dosage unit is between 10 mg to 1000 mg, preferably between 30 mg to 500 mg, more preferably between 40 mg to 300 mg and most preferably between 50 mg to 100 mg of PS.

It should be noted that the PS preparation of the invention may also comprise other phospholipids, such as phosphatidylcholine (PC), phosphatidylethanolamine (PE), phosphatidyl-inositol (PI), phosphatidylglycerol (PG) and phosphatidic acid (PA), to which fatty acid acyls are covalently attached (bonded) at either or both of the sn-1 or sn-2 positions of the glycerol moiety of the phospholipid. The fatty acid conjugation profile of any of the above-noted polar lipids may be the same as, or different from, the fatty acid conjugation profile of PS, as disclosed herein.

The PS preparation of the invention is prepared from a natural, synthetic or semi-synthetic source or any combinations thereof. In an embodiment of the present invention, said natural source is derived from any one of plant (such as for example soy or sunflower), non-mammalian animal (such as for example krill, fish (such as for example Herring and blue Whiting)), or microorganism (such as for example bacteria) source or any combinations thereof.

Methods for preparing the PS powder preparation of the invention include, but are not limited to:

1. Bi-phasic transphosphatidylation reaction in which the reaction is carried out in a system containing aqueous and organic mediums. Lecithin is being dissolved in the organic phase while other ingredients such as phospholipase enzyme and serine are dissolved in water (as described in U.S. Pat. No. 5,700,668).
2. Monophasic transphosphatidylation reaction in which the reaction is carried out in an aqueous medium, the lecithin is dispersed during the reaction and other ingredients such as phospholipase enzyme and serine are dissolved in water (as described in U.S. Pat. No. 6,492,146 and WO05068644).

Preferably, following the transphosphatidylation reaction additional purification steps using a solvent are added to the procedure. Preferably the solvent is an alcohol solvent, more preferably an alcohol solvent with C1-C6 and most preferably an alcohol solvent with C2-C3. The solid is being dispersed with the solvent and stirred for one hour, preferably two hours and more preferably three hours and separation can be achieved using a variety of filtration techniques including but not limited to basket centrifuge, bowl centrifuge, decanter, etc., the solids are being washed more than once, preferably twice, more preferably three times and most preferably four times.

The obtained powder PS is dried using one of the following non-limiting technologies: vacuum oven, spray dryer, drum dryer, double cone dryer, paddle dryer, etc. and milled, optionally in one of the following non-limiting examples: Pin mill, Hammer mill, Cone mill, Jet mill, Boll mill, etc.

Preferably, following milling, the obtained PS powder is going through a sieving stage using one of the following non limiting technologies: air classifier, vibrating sieve, sifter, etc. to obtain PS powder preparation with predetermined particle size.

In one embodiment, powder PS is being sieved using 500 microns screen, preferably 400 microns screen, more preferably 350 microns or 300 microns, even more preferably 250 microns or 200 microns and most preferably 150 microns.

In another one of its aspects the invention provides a method of improving general health, cognitive functions and/or development, and/or improving and/or preventing a condition in a subject suffering from a cognitive disease or disorder comprising administering to a subject in need thereof the PS preparation of the invention.

The invention further provides a use of a preparation of the invention for the manufacture of a nutraceutical or a medical food for improving a condition in a subject suffering from a cognitive disease or disorder.

The term "cognitive disease or disorder" as used herein should be understood to encompass any cognitive disease or disorder. Non-limiting examples of such a cognitive disease or disorder are Attention Deficit Disorder (ADD), Attention Deficit Hyperactivity Disorder (ADHD), dyslexia, age-associated memory impairment, learning disorders, amnesia, mild cognitive impairment, cognitively impaired non-demented, pre-Alzheimer's disease, Alzheimer's disease, Parkinson's disease, pre-dementia syndrome, dementia, age related cognitive decline, cognitive deterioration, moderate mental impairment, mental deterioration as a result of aging, conditions that influence the intensity of brain waves and/or brain glucose utilization, stress, anxiety, depression, behavior disorders, concentration and attention impairment, mood deterioration, general cognitive and mental well-being, neurodegenerative disorders, hormonal disorders or any combinations thereof. In a specific embodiment, the cognitive disorder is memory impairment.

The term "improving a condition in a subject suffering from a cognitive disease or a cognitive disorder" as used herein should be understood to encompass: ameliorating undesired symptoms associated with a disease, disorder, or pathological condition; preventing manifestation of symptoms before they occur; slowing down progression of a disease or disorder; slowing down deterioration of a disease or disorder; slowing down irreversible damage caused in a progressive (or chronic) stage of a disease or disorder; delaying onset of a (progressive) disease or disorder; reducing severity of a disease or disorder; curing a disease or disorder; preventing a disease or disorder from occurring altogether (for example in an individual generally prone to the disease) or a combination of any of the above. For example, in a subject suffering from memory impairment, for example as a result of Alzheimer's Disease, symptoms including deterioration of spatial short-term memory, memory recall and/or memory recognition, focused and sustained attention, learning, executive functions and/or mental flexibility are improved by use of a lipid preparation of the invention.

According to one embodiment the PS preparation of the invention is dry blended with a powder nutraceutical prior to mixing the nutraceutical with water.

According to another embodiment, the powder PS of the invention is blended with water based nutraceutical.

In yet another aspect of the invention, the PS preparation is being added to chewable matrix, such as candy or gummy.

The numerical values provided herein are representative of those employed by the inventors for practicing and describing the preferred embodiments of the present invention. It should be appreciated that while these values are exemplary of preferred embodiments for practicing and describing the invention, those skilled in the art, in light of the present disclosure, will recognize that these values are not intended to necessarily require exact numerical precision and may be subject to a reasonable degree of variability without departing from the spirit and intended scope of the invention.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

Example 1

Production of PS powder using a monophasic reaction (sample No. 1). 140 gr of an emulsion containing ethanol purified soy lecithin in water was mixed with a solution containing 41 gr L-serine, 35 ml acetate buffer and 0.55 gr phospholipase-D enzyme and stirred at 40° C. After 36 hours of stirring, the solution was filtered through a Buchner filter in order to remove all water soluble components. The solids were dispersed in 140 ml purified water for 30 minutes and filtered once again. The wet solids were dried in a vacuum dryer to obtain dry PS powder with PS concentration of 58.8% measured using HPLC. Dry powder was milled together with 2% silicon dioxide to obtain free flowing powder in which more than 20% (w/w) of the powder had particle size above 500 microns.

Example 2

Sieving sample No. 1 (production of sample No. 2). Sample No. 1 was sieved through 250 microns screen to obtain powder in which 97% (w/w) of the powder had particle size of 250 microns or less.

Example 3

Purification of sample No. 1 using alcohol solvents (production of sample No. 3). 10 gr from sample No. 1 (before drying) were dispersed in 40 ml ethanol and the solution was stirred for 30 minutes. The solution was filtered through a Buchner filter to separate between the solids and filtrate. The solids were collected from the filter and the same process was repeated two more times. Wet solids were dried in a vacuum dryer to obtain dry PS powder. Dry powder was milled together with 2% silicon dioxide to obtain free flowing powder in which more than 20% (w/w) of the powder had particle size above 500 microns.

Example 4

Sieving sample No. 3 (production of sample No. 4). Sample No. 3 was sieved through 250 microns screen in order to obtain powder in which 97% (w/w) of the powder had particle size of 250 microns or less.

Example 5

Production of PS powder using a bi-phasic reaction (sample No. 5). 40 gr of ethanol purified soy lecithin were dissolved in 400 ml hexane and 26.4 gr MCT oil, the solution was concentrated up to total dryness. 132 ml hexane and 50 ml ethyl acetate were added to create organic phase. 112 ml purified water, 52 gr L-serine, 36 ml acetate buffer and 2 gr phospholipase-D enzyme were mixed together to create the aqueous phase. The two phases were stirred for 36 hours at 40° C. After stopping stirring, two phases were formed. The lower phase was removed and the upper phase was concentrated up to total dryness. The oil was mixed with 500 ml of ethanol for 30 minutes and filtered through a Buchner filter in order to create powder. The cake was collected and re-washed with additional 500 ml. The re-wash was repeated once more in the same manner. Wet solids were dried in a vacuum dryer to obtain dry PS powder. Dry powder was milled together with 2% silicon dioxide to obtain free flowing powder in which more than 20% (w/w) of the powder had particle size above 500 microns.

Example 6

Sieving sample No. 5 (production of sample No. 6). Sample No. 5 was sieved through 250 microns screen to obtain powder in which 97% (w/w) of the powder had particle size of 250 microns or less.

Example 7

Floating and sedimentation properties of dry blends of different PS powders with a nutritional composition (Similac®) following dispersion. 100 mg PS powder from each sample (1-6) were blended with 9.9 gr commercial infant formula (Similac®) by a gentle mixing process. The blended material was dispersed in 60 ml purified water. Table No. 1 describes the floating and sedimentation properties of the dispersed blends. Advantageously, samples No. 2, 4 and 6 resulted in a solution with improved homogenous appearance. The homogenous appearance of the solution containing sample No. 4 was improved even in comparison with solutions containing samples No. 2 or 6.

TABLE 1

Appearance of nutraceutical containing PS powder of samples 1-6

| Sample No. | Floating particles | Sedimentation | Homogenous appearance |
|---|---|---|---|
| 1 | + | + | − |
| 2 | − | + | + |
| 3 | + | + | − |
| 4 | − | − | ++ |
| 5 | + | + | − |
| 6 | + | − | + |

Example 8

Production of gummies containing powder PS. Gummies were produced using conventional methods as described in Handbook of food science, technology and engineering, volume 3, Chapter 140 page 26. PS powder dispersed in water was added prior to the gelation of the pectin (just before the addition of citric acid).

Example 9

Texture analysis of gummies containing PS powder of the invention in comparison with conventional PS powder. Gummies, produced as described in example 8 in a lab scale, and containing either 4.5% PS powder according to the invention (sample No. 4) or other PS (sample No. 3), were analyzed for their appearance and stability. As demonstrated in Table 2, gummies containing PS powder of the invention had better appearance and stability in comparison with gummies containing other PS powder composition.

TABLE 2

Appearance and stability of gummies containing PS powder of samples No. 3 or 4

| | Appearance | Hardness |
|---|---|---|
| Gummies containing the PS powder of sample No. 4 | Uniform | Stable and elastic during storage |
| Gummies containing the PS powder of sample No. 3 | Non uniform | Cracks were observed during storage |

The invention claimed is:

1. A process for the preparation of a phosphatidylserine powder composition comprising the steps of:

(i) performing an aqueous monophasic transphosphatidylation of lecithin in a solution comprising a phospholipase enzyme and serine;

(ii) purification with an alcohol solvent;

(iii) drying;

(iv) milling; and (v) sieving;

wherein at least 95% (w/w) of the phosphatidylserine powder has a particle size of 250 microns or less, and wherein the phosphatidylserine powder composition contains at least 20% w/w phosphatidylserine out of the composition.

2. The process of claim 1, wherein the lecithin is from a natural, synthetic, or semi-synthetic source, or a combination thereof.

3. The process of claim 2, wherein the lecithin is from a natural source.

4. The process of claim 3, wherein the natural source is derived from plants, non-mammalian animals, or microorganisms.

5. The process of claim 4, wherein the natural source is soy, sunflower, or a combination thereof.

6. The process of claim 1, wherein alcohol solvent used in the purification step comprises a $C_1$-$C_6$ alcohol.

7. The process of claim 6, wherein alcohol solvent used in the purification step comprises a $C_2$-$C_3$ alcohol.

8. The process of claim 7, wherein alcohol solvent used in the purification step comprises ethanol.

9. The process of claim 1, wherein the purification step further comprises dispersal in the alcohol solvent followed by separation of the alcohol solvent.

10. The process of claim 1, wherein the milling step comprises pin, hammer, cone, jet, or ball milling, or a combination thereof.

11. The process of claim 1, wherein the milling step comprises milling with silicon dioxide.

12. The process of claim 1, wherein the phosphatidylserine powder preparation contains at least 30% w/w phosphatidylserine out of the composition.

13. The process of claim 1, wherein at least 97% (w/w) of the phosphatidylserine powder composition has a particle size of 250 microns or less.

14. The process of claim 1, wherein the powder composition when mixed in water without processing by high pressure homogenization, disperses more homogeneously and demonstrates reduced sedimentation compared to a PS preparation in which more than 20% (w/w) of the PS preparation has a particle size of above 500 microns.

15. The process of claim 1, wherein the phosphatidylserine powder composition is mixed with a powder nutritional, nutraceutical, or pharmaceutical composition to form a mixture that when mixed with water without processing by high pressure homogenization, the mixture disperses more homogeneously and reduces sedimentation compared to a mixture of the powder nutritional, nutraceutical, or pharmaceutical composition and a PS preparation in which more than 20% (w/w) of the PS preparation has a particle size of above 500 microns.

16. The process of claim 1, wherein the phosphatidylserine powder composition when mixed without processing by high pressure homogenization with a liquid nutritional, nutraceutical, or pharmaceutical composition disperses more homogeneously and demonstrates reduced sedimentation compared to a PS preparation in which more than 20% (w/w) of the PS preparation has a particle size of above 500 microns.

* * * * *